United States Patent
Gopinathan et al.

(10) Patent No.: US 7,753,845 B2
(45) Date of Patent: *Jul. 13, 2010

(54) TELE-DIAGNOSTIC DEVICE

(75) Inventors: Govindan Gopinathan, Oradell, NJ (US); Arthur R. Tilford, Yorba Linda, CA (US)

(73) Assignee: INEEDMD.com, Inc., Great Neck, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 10/400,850

(22) Filed: Mar. 27, 2003

(65) Prior Publication Data

US 2005/0075541 A1 Apr. 7, 2005

Related U.S. Application Data

(60) Division of application No. 09/741,283, filed on Dec. 19, 2000, now Pat. No. 6,540,673, which is a continuation of application No. 09/084,647, filed on May 26, 1998, now Pat. No. 6,224,548.

(51) Int. Cl.
*A61B 5/00* (2006.01)

(52) U.S. Cl. .................. 600/300; 600/301; 600/485; 600/500; 600/508

(58) Field of Classification Search .......... 600/300, 600/301
See application file for complete search history.

(56) References Cited

U.S. PATENT DOCUMENTS

| | | |
|---|---|---|
| 206,474 A | 7/1878 | Morel |
| 2,621,657 A | 12/1952 | Leech |
| 3,508,541 A | 4/1970 | Westbrook et al. |
| 3,659,614 A | 5/1972 | Jankelson |
| 3,845,771 A | 11/1974 | Vise |
| 3,888,240 A | 6/1975 | Reinhold, Jr. et al. |
| 4,014,323 A | 3/1977 | Gilmer et al. |

(Continued)

FOREIGN PATENT DOCUMENTS

EP 0 459 239 A2 12/1991

(Continued)

OTHER PUBLICATIONS

Hajime Murakami et al., "Telemedicine Using Mobile Satellite Communication", IEEE Transactions on Biomedical Engineering, vol. 41, No. 5, May 1994. pp. 488-497.

(Continued)

*Primary Examiner*—Robert L Nasser
(74) *Attorney, Agent, or Firm*—Brooks Kushman P.C.

(57) ABSTRACT

A system (10) for collecting a plurality of diagnostic information and transmitting the diagnostic information to a remote location. The system (10) comprises a glove member (12) adaptable to be worn on a person's hand and an interface unit (20) in electrical communication with the glove member (12). The interface unit (20) is capable of transmitting information to, and receiving information from, a remote location. The glove member (12) comprises a palm portion (1), a wrist portion (3) and five phalange portions (5-13). The glove member (12) further comprises an EKG diagnostic device, a blood pressure and pulse rate diagnostic device (54) and a temperature device (64). The glove member (12) may also further comprise a % $O_2$ diagnostic device (70) and an auscultation device (80).

25 Claims, 3 Drawing Sheets

U.S. PATENT DOCUMENTS

| | | | |
|---|---|---|---|
| 4,016,868 A | 4/1977 | Allison | |
| 4,033,334 A | 7/1977 | Fletcher et al. | |
| 4,062,364 A | 12/1977 | Masaki | |
| 4,230,127 A | 10/1980 | Larson | |
| 4,381,012 A | 4/1983 | Russek | |
| 4,419,998 A * | 12/1983 | Heath | 600/391 |
| 4,510,939 A | 4/1985 | Brenman et al. | |
| 4,556,063 A | 12/1985 | Thompson et al. | |
| 4,583,547 A | 4/1986 | Granek et al. | |
| 4,608,987 A | 9/1986 | Mills | |
| 4,662,378 A | 5/1987 | Thomis | |
| 4,698,848 A | 10/1987 | Buckley | |
| 4,706,679 A | 11/1987 | Schmidt et al. | |
| 4,709,704 A | 12/1987 | Lukasiewicz | |
| 4,765,343 A | 8/1988 | Brenman et al. | |
| 4,974,607 A | 12/1990 | Miwa | |
| 5,007,427 A | 4/1991 | Suzuki et al. | |
| 5,224,479 A | 7/1993 | Sekine | |
| 5,345,934 A | 9/1994 | Highe et al. | |
| 5,353,793 A | 10/1994 | Bornn | |
| 5,429,140 A * | 7/1995 | Burdea et al. | 600/587 |
| 5,431,170 A | 7/1995 | Mathews | |
| 5,441,047 A | 8/1995 | David et al. | |
| 5,442,729 A | 8/1995 | Kramer et al. | |
| 5,454,779 A * | 10/1995 | Lurie et al. | 601/43 |
| 5,462,051 A * | 10/1995 | Oka et al. | 600/300 |
| 5,465,727 A | 11/1995 | Reinhold, Jr. | |
| 5,511,546 A * | 4/1996 | Hon | 600/490 |
| 5,562,803 A * | 10/1996 | Wang et al. | 162/5 |
| 5,564,429 A | 10/1996 | Bornn et al. | |
| 5,619,991 A | 4/1997 | Sloane | |
| 5,626,151 A | 5/1997 | Linden | |
| 5,640,953 A | 6/1997 | Bishop et al. | |
| 5,666,404 A | 9/1997 | Ciccotelli et al. | |
| 5,670,944 A | 9/1997 | Myllymaki | |
| 5,687,738 A | 11/1997 | Shapiro et al. | |
| 5,701,904 A | 12/1997 | Simmons et al. | |
| 5,704,364 A | 1/1998 | Saltzstein et al. | |
| 5,730,140 A | 3/1998 | Fitch | |
| 5,738,104 A | 4/1998 | Lo et al. | |
| 5,758,095 A | 5/1998 | Albaum et al. | |
| 5,771,001 A | 6/1998 | Cobb | |
| 5,771,891 A | 6/1998 | Gozani | |
| 5,827,180 A * | 10/1998 | Goodman | 600/300 |
| 5,855,550 A | 1/1999 | Lai et al. | |
| 5,877,675 A | 3/1999 | Rebstock | |
| 5,902,234 A | 5/1999 | Webb | |
| 5,967,559 A | 10/1999 | Abramowitz | |
| 6,007,569 A * | 12/1999 | Frenkel et al. | 607/88 |
| 6,022,321 A | 2/2000 | Amano et al. | |
| 6,078,907 A | 6/2000 | Lamm | |
| 6,102,856 A * | 8/2000 | Groff et al. | 600/301 |
| 6,149,586 A * | 11/2000 | Elkind | 600/300 |
| 6,217,523 B1 | 4/2001 | Amano et al. | |
| 6,224,548 B1 | 5/2001 | Gopinathan et al. | |
| 6,248,064 B1 | 6/2001 | Gopinathan et al. | |
| 6,285,991 B1 | 9/2001 | Powar | |
| 6,341,229 B1 | 1/2002 | Akiva | |
| 6,364,842 B1 * | 4/2002 | Amano et al. | 600/485 |
| 6,516,289 B2 | 2/2003 | David | |
| 6,540,673 B2 * | 4/2003 | Gopinathan et al. | 600/300 |
| 6,560,473 B2 | 5/2003 | Dominguez | |
| 6,589,171 B2 | 7/2003 | Keirsbilck | |
| 6,595,918 B2 * | 7/2003 | Gopinathan et al. | 600/300 |
| 6,611,705 B2 | 8/2003 | Hopman et al. | |
| 7,112,175 B2 * | 9/2006 | Gopinathan et al. | 600/508 |
| 7,435,222 B2 * | 10/2008 | Gopinathan et al. | 600/508 |

FOREIGN PATENT DOCUMENTS

| | | |
|---|---|---|
| EP | 0 706 776 A1 | 4/1996 |
| EP | 0 761 160 A1 | 3/1997 |
| EP | 0 770 349 A1 | 5/1997 |
| EP | 0 880 936 A2 | 12/1998 |
| WO | WO 84/02459 A1 | 7/1984 |
| WO | WO 98/04182 A2 | 2/1998 |
| WO | WO 98/17172 A2 | 4/1998 |

OTHER PUBLICATIONS

Gail Wyman, "The Maturing of Telemedicine Technology", Health Systems Review, Little Rock: Sep./Oct. 1994, vol. 27, Iss. 5; p. 57.

Dorothy J. Fishman, "Telemedicine: Bringing the Specialist to the Patient", Nursing Management, Chicago: Jul. 1997, vol. 28, Iss. 7; p. 30.

* cited by examiner

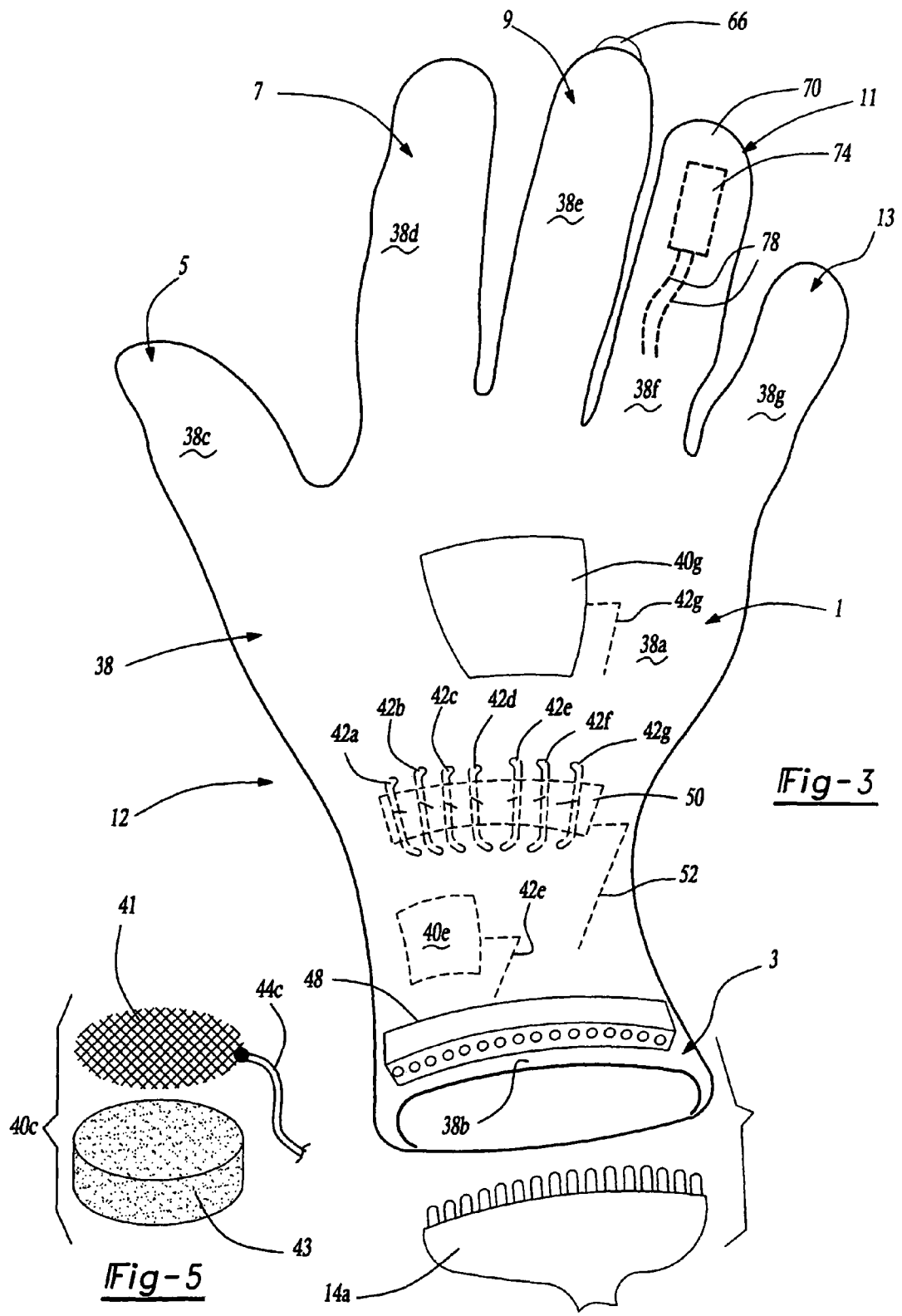

TELE-DIAGNOSTIC DEVICE

This application is a divisional of U.S. application Ser. No. 09/741,283, filed Dec. 19, 2000, now U.S. Pat. No. 6,540,673, which is a continuation of U.S. application Ser. No. 09/084,647, filed May 26, 1998, now U.S. Pat. No. 6,224,548

TECHNICAL FIELD

This invention relates to a system, and a probe for use with the system, for obtaining a plurality of medical diagnostic information. In particular, the present invention relates to a system and probe for use with the system, for gathering cardiac-related diagnostic information and transmitting the information to a remote location, such as a medical monitoring command center.

BACKGROUND

Doctor-patient relationships are as old as human civilization itself. Over the centuries this relationship has undergone, surprisingly enough, very little change. One way or another the patient and the doctor came into contact with each other in person. This process was called a patient visit or doctor visit, as the case may be. From the very beginning of this patient-doctor interaction, a certain format and structure evolved and later this was laid down as a stipulated discipline in the practice of medicine. The doctor interrogates the patient in a methodical way, the patient provides the answers, which in fact, is the history of the evolution of the patient's illness. The doctor then examines the patient, makes crucial observations and gathers diagnostic data, or information, which are the fingerprints of the illness the patient is suffering from. An intellectual process ensues in the doctor's mind, where he correlates the history of the illness with the diagnostic information he gathered and the conclusion he arrives at, essentially, is the diagnosis of the patient's malady.

Over the years, innovations like the telegraph, the telephone, fax machines and of late, the e-mail and the Internet, has enhanced the patient-doctor relationship quite substantially. These innovations have curtailed the need for more frequent personal visits, by the patient or the doctor, as the case may be. Doctors on their part however, always prefer to speak to the patient and gather vital diagnostic information personally by themselves, even when the patient is located remotely from the doctor. Thus, it would be desirable to be able to gather and transmit a plurality of diagnostic information and converse with a doctor, or medical professional, at a remote location. Moreover, it would be desirable to provide a single apparatus which could collect a plurality of diagnostic information.

Moreover, it has been observed that at least about one third of the patients who visit emergency rooms (ER) across the country, do not have emergency problems. They visit the ER because they believed that they are having a heart attack or another medical emergency, or they prefer to use the emergency room instead of paying a visit to their general practitioner (GP) or primary care physician (PCP). These unnecessary visits to the ER sometimes prove to be quite costly to the patients and/or their healthcare underwriter in more ways than one. As a first example, if someone had epigastric pain from indigestion, a visit to the GP or PCP would cost, at the most about $75.00. A visit to any ER for the same purpose could cost upwards of about $500. Also, while medical professionals tend to a patient not actually requiring emergency treatment, another patient who actually could benefit from emergency treatment may go untreated. If the patient has been provided with a means for gathering and transmitting a plurality of diagnostic information and for conversing with a medical professional at a remote location, the patient would be able to communicate with, and transmit diagnostic information to, a medical professional at a monitoring center (MC) or an ER, prior to visiting an ER. The medical professional, being able to communicate with and review a plurality of the patient's diagnostic information, can quickly decide if this patient has an emergency pr not, and the medical professional is also in a position to periodically monitor this patient, over a period of several hours. This could be done at a cost which would be a fraction of an ER visit and would free up ER's to care for patients actually requiring emergency treatment.

Once we look beyond the urban areas, especially in large central and mid-western states, patients live hundreds of miles away from their doctors. Follow-up of these patients is a problem. Providing transportation to sick people is a lofty idea, but in practice is quite expensive. A means for gathering and transmitting a plurality of diagnostic information to, and for communicating with, a remote location provides the medical community with a formidable, cost-effective tool.

A means for gathering and transmitting a plurality of diagnostic information to, and for communicating with, a remote location, in addition to providing a means for preventing unnecessary ER visits, can also be helpful in providing emergency care to patients who, for all practical purposes, cannot get to an ER, such as airplane or boat passengers. The medical professional at a remote location can monitor the patient's diagnostic information and be able to communicate with the patient or persons by the patient's side for the purpose of providing medical instructions to the patient and/or persons.

In the prior art, there are devices which gather and transmit diagnostic information (such as EKG) to a remote location. However, these prior art devices are limited in the amount and type of diagnostic information they can gather and transmit. Moreover, these prior art devices are typically complicated and difficult to use. Accordingly, it would be desirable to provide a simple to use means for gathering and transmitting a plurality of diagnostic information and for communicating with a remote location.

If a patient were suffering from symptoms consistent with a heart attack, in order to provide an accurate diagnosis and/or course of action, the examining medical professional would preferably gather the following minimum diagnostic information: Electrocardiogram (EKG); Blood Pressure (BP); Pulse; and body temperature. In many instances, a medical professional would also prefer to be able to determine the percentage of oxygen saturation in the blood (% $O_2$); and auscultation of the patient's heart and lungs. Also, the examining medical professional would prefer to communicate with the patient or person(s) by the patient's side to aid in gathering diagnostic information and/or to provide medical instructions. Accordingly, it would be desirable to provide an inexpensive and easy to use probe device which could gather and transmit to a remote location the above-mentioned diagnostic information and also provide the ability to allow oral communication with a remote location.

DISCLOSURE OF THE INVENTION

An object of the present invention is to provide an inexpensive and easy to use probe which could gather and transmit plurality of diagnostic information to a remote location.

In carrying out the above object, a system for collecting a plurality of diagnostic information and transmitting the diagnostic information to a remote location is provided. The system comprises a glove member adaptable to be worn on a person's hand and an interface unit in electrical communication with the glove member. The interface unit is capable of transmitting information to, and receiving information from, a remote location. The glove member comprises a palm portion, a wrist portion and five phalange portions. The glove member further comprises an EKG diagnostic device, a blood pressure and pulse rate device and a temperature device. Also, the glove member could have a % $O_2$ device, as well as an auscultation device.

BRIEF DESCRIPTION OF THE DRAWINGS

FIG. 3 is a plan view of a second side of an apparatus of the present invention;

FIG. 4 is a schematic diagram of the circuit of the interface unit shown in FIG. 1; and FIG. 5 is an exploded view of an EKG sensor used in FIGS. 2 and 3.

BEST MODE FOR CARRYING OUT THE INVENTION

The present invention relates to a system, and a diagnostic probe for use with the system, for obtaining a plurality of medical diagnostic information. In particular, the present invention relates to a system, a diagnostic probe device and an information transmission device for use with the system, for gathering cardiac related diagnostic information and transmitting the information to a remote location, such as a medical monitoring command center.

Figure 1:
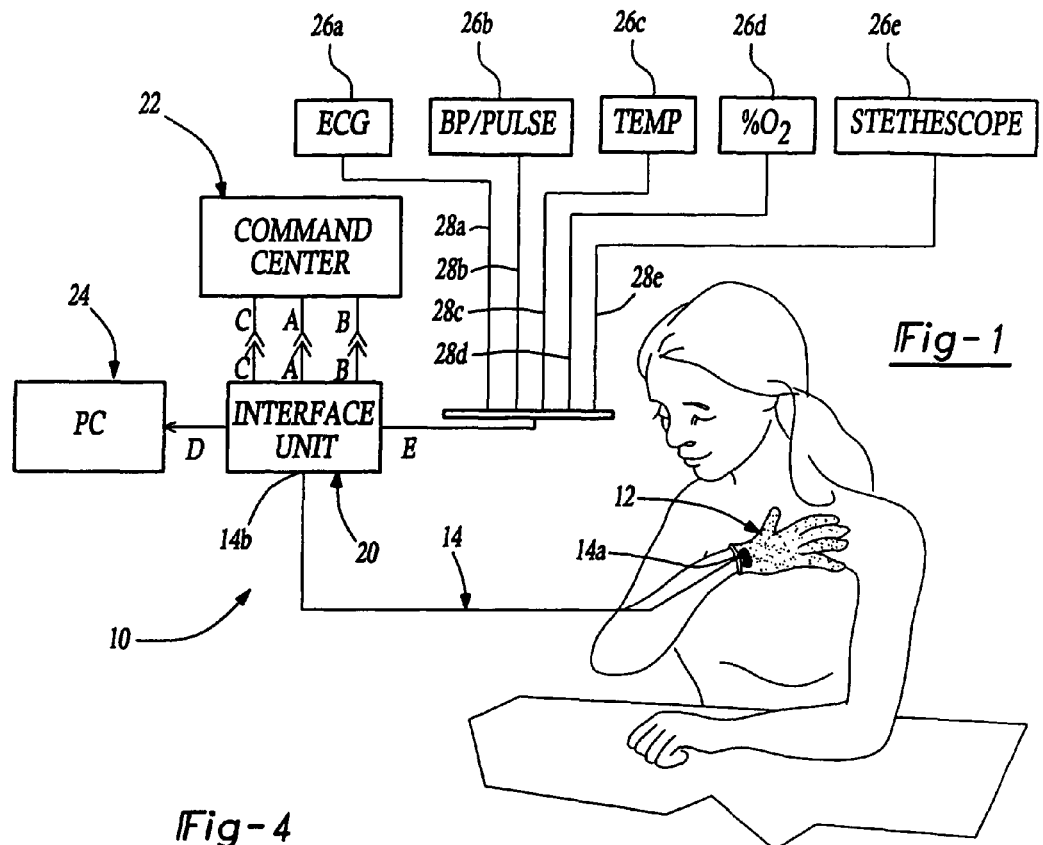
FIG. 1 is a schematic view of the system of the present invention.

As representative of the present invention, FIG. 1, illustrates a system 10 for gathering, and transmitting, to a remote location a plurality of diagnostic information.

The system 10 includes a glove probe 12. The glove probe 12 is a unitary member which is adaptable to be worn over a person's hand. The glove probe 12 includes a plurality of medical diagnostic probes which gather diagnostic signals, as will be explained in more detail below. The glove probe 12 is connected via a cable 14 to an interface unit 20 and, thus communicates with, and is capable of transmitting diagnostic signals, or information, from the medical diagnostic probes to the interface unit. The interface unit 20 communicates with a remote command center 22 via a telephone wire or fiber A, a satellite connection B, or a radio wave connection C. The interface unit 20 alternatively communicates with a personal computer (PC) 24 via an interface connection D. The interface unit 20 also communicates with a plurality of local diagnostic readout apparatuses 26a, 26b, 26c, 26d, and 26e via an interface connection E via a plurality of interface connections, 28a, 28b, 28c, 28d, and 28e, respectively. The diagnostic readout apparatuses 26a-e are preferably an electrocardiogram (EKG) readout; a blood pressure (BP) and pulse readout, a % $O_2$ oxygen readout, a temperature readout, and a stethoscope, respectively.

Figure 2:
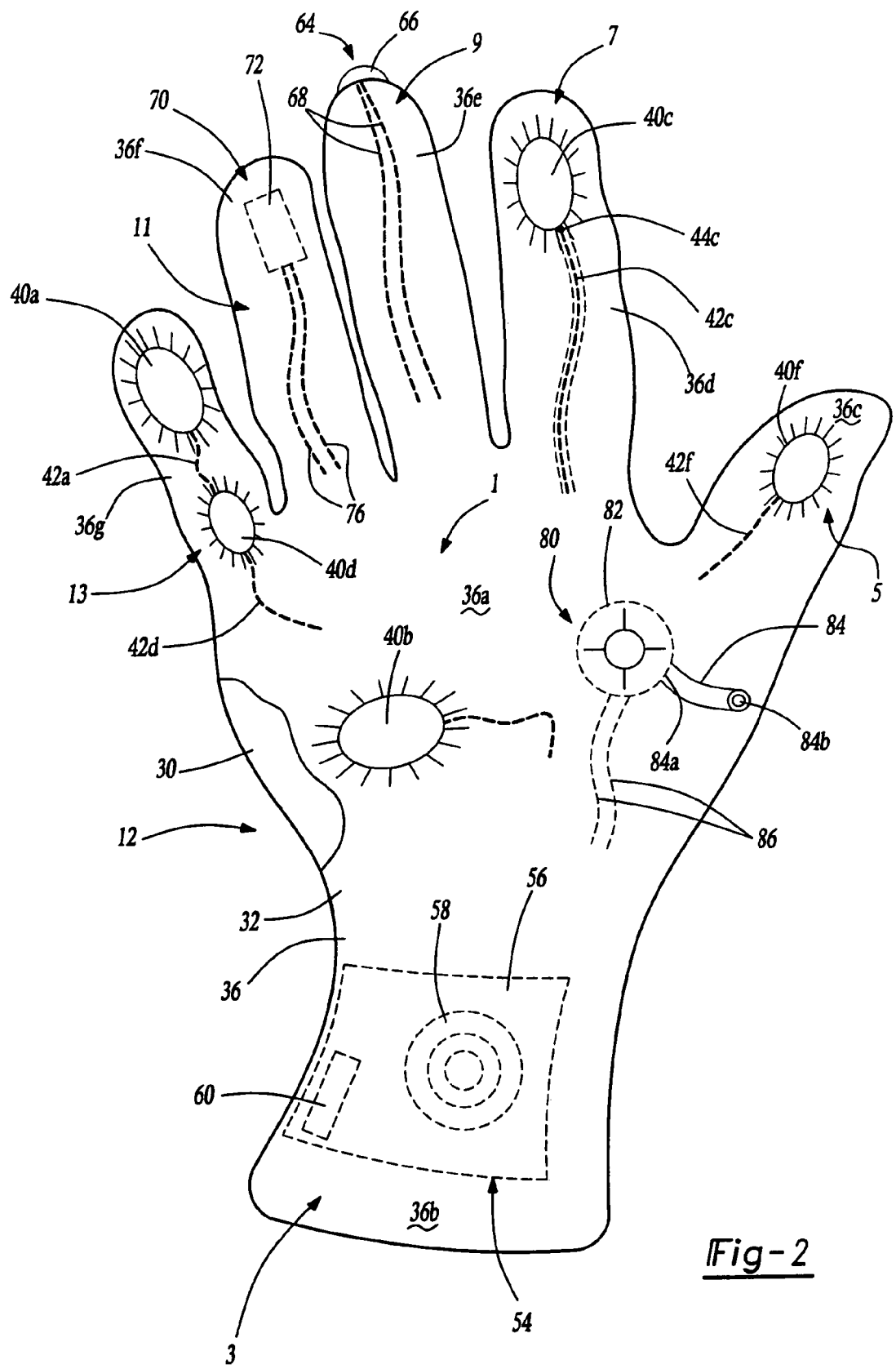
FIG. 2 is a plan view of a first side of an apparatus of the present invention.

Referring to FIG. 2, the glove probe 12 comprises a first glove layer 30 and a second glove layer 32 secured to the first glove layer such that the second glove layer overlies most of the first glove layer. The first glove layer 30 is preferably made of a cloth of natural or synthetic fibers. The second layer 32 is preferably made of a rubber or rubber-like material.

The glove probe 12 includes a palm portion 1, a wrist portion 3, a thumb phalange portion 5, an index finger phalange portion 7, a middle finger phalange portion 9, a ring finger phalange portion 11 and a pinky finger phalange portion 13. The glove probe 12 further includes a palmar side 36 (FIG. 2) and a dorsal side 38 (FIG. 3). The palmar side 36 (FIG. 2) includes a palmar palm portion surface 36a, a palmar wrist portion surface 36b, a palmar thumb phalange portion surface 36c, a palmar index finger phalange portion surface 36d, a palmar middle finger phalange portion surface 36e, a palmar ring finger phalange portion surface 36f and a palmar pinky finger phalange portion surface 36g. The dorsal side 38 (FIG. 3) includes a dorsal palm portion surface 38a, a dorsal wrist portion surface 38b, a dorsal thumb phalange portion surface 38c, a dorsal index finger phalange portion surface 38d, a dorsal middle finger phalange portion surface 38e, a dorsal ring finger phalange portion surface 38f and a dorsal pinky finger phalange portion surface 38g.

As discussed previously, the glove probe 12 contains a plurality of medical diagnostic devices. In the embodiment shown in FIGS. 2 and 3, the glove probe 12 contains an EKG diagnostic device, a blood pressure and pulse rate device 54, a temperature device 64, a % $O_2$ device 70 and an auscultation device 80.

The EKG device is capable of measuring the EKG currents of the heart muscle and preferably includes a plurality of sensors 40a (FIG. 2), 40b, 40c, 40d, 40e (FIG. 3), 40f (FIG. 2) and 40g (FIG. 3) which are secured to the first layer 30 (FIG. 2) of the glove probe 12. An exemplary sensor 40c is shown in FIG. 5. Each of the sensors 40a-40g includes a stainless-steel screen 41 and an EKG gelly sponge 43 disposed between the screen and, preferably, the first layer 30 (FIG. 5). Sensors 40a, 40b, 40c, 40d and 40f (FIG. 2) are provided on the palmer side 36 of the glove probe 12. Sensors 40e and 40g (FIG. 3) are provided on the dorsal side 38 of the glove probe 12. Sensors 40a-40d, 40f and 40g preferably extend through, or are not covered by, the second layer 32 so that they are exposed to the environment. Sensor 40e faces the palmer side 36 of the glove probe 12.

More specifically, sensor 40a (FIG. 2) is positioned on the tip portion of the palmar pinky finger phalange portion surface 36e of the glove probe 12. Sensor 40b is positioned on the left side of the palmar palm portion surface 36a of the glove probe 12. Sensor 40c is positioned on the upper portion of the palmar index finger phalange portion surface 36d of the glove probe 12. Sensor 40d is positioned on the base portion of the palmar pinky finger phalange portion surface 36g, between sensor 40a and sensor 40b, of the glove probe 12. Sensor 40e (FIG. 3) is located on the left side of the dorsal wrist portion surface 36b of the of the glove probe 12. Sensor 40f (FIG. 2) is positioned on the palmar thumb phalange portion surface 36c of the glove probe 12. Sensor 40g (FIG. 3) is positioned on the dorsal palm portion surface 38a of the glove probe 12.

Each of the sensors 40a-40g are connected to a wire 42a-42g, respectively, which extends between and electrically connects a respective one of the sensors 40a-40g with a female connection plug 48, which is preferably provided on the dorsal side of the glove probe 12. Each wire 42a-42g is preferably disposed between the first and second layers 30 and 32 of the glove probe 12, and is preferably secured to the first layer 30. Each wire 42a-42g is preferably shielded and has a powdered-iron bead 44c (FIG. 5), such as Part No. T12-41 from Amidon Associates in Santa Ana, Calif. (shown only with respect to sensor 40c) disposed adjacent to its respective sensors 40a-40g to help prevent the detection of unwanted noise.

The glove probe 12 includes a ground strip 50 (FIG. 3) which is preferably positioned on the palm portion 3 of the dorsal side 38 between the first and second layers 30 and 32. Each wire 42a-42g is connected to the ground strip 50, preferably, via each respective wire shield. The ground strip 50 is connected to a wire 52, which extends between and connects the ground strip 50 to the female connection plug 48. The ground strip 50 functions to bring existing electromagnetic forces (EMF) noise to a single electrical voltage point for removal.

The blood pressure device 54, which is capable of measuring systolic and diastolic blood pressure and pulse rate signals, is preferably secured to the first layer 30 of the glove probe 12 between the first layer and the second layer 32 on the wrist portion 3 of the dorsal side 38 of the glove probe. The blood pressure device 54 preferably includes an expandable air bladder 56 defining a chamber for accommodating air or another suitable inflation fluid, an acoustical coupler 58 in the chamber and an air tube 60. The air tube 60 extends between and provides fluid and audio communication between the chamber of the air bladder 56 and the female connection plug 48. The acoustical coupler 58 is capable of collecting the sound waves in the air bladder 56 and directing the sound waves towards, and through, the air tube 60. The blood pressure device 54 is preferably made of parts similar, or identical, to parts of the UB-302 Systolic/Diastolic (Pulse) Digital Blood Pressure monitor from A+D Engineering Inc., of Milpitas, Calif.

The temperature device 64 is capable of measuring temperature signals and preferably includes a thermistor 66. The thermistor 66 is preferably positioned on the tip of the middle finger phalange portion 9. The thermistor 66 is preferably secured to the first layer 30 and extends through the second layer 32. The temperature device 64 includes a pair of wires 68 which extend between and electrically connect the thermistor 66 and the female connection plug 48. The temperature device 64 is preferably made of parts similar, or identical, to parts of the Cole-Parmer E-08402-00 thermometer and Generic thermistor E-08459-10 from Cole-Parmer Instrument Company of Vernon Hills, Ill.

The % $O_2$ device 70 is capable of measuring the percent oxygen saturation in the blood (% $O_2$) signals and preferably includes a red (600-660 nm) and infra-red (880-1000 nm) LED emitter 72 and an LED (600-1000 nm) sensor 74. The LED emitter 72 is preferably secured to the inner surface of the first layer 30 on the palmar side 36 of ring finger phalange portion 11 of the glove probe 12 and the LED sensor 74 is preferably secured to the inner surface on the dorsal surface 38 of the ring finger phalange portion 11 of the glove probe such that the LED emitter faces the LED sensor. The LED emitter 72 is connected to a pair of wires 76 which extend between and electrically connect the LED emitter and the female connection plug 48. The LED sensor 74 is connected to a pair of wires 78 which extend between and electrically connect the LED sensor and the female connection plug 48. The % $O_2$ device 70 is preferably made of parts similar, or identical, to parts of the Nonin Onyx blood flow and oxygen % reader, model No. 8500M from Nonin Medical, Inc., of Plymouth, Minn.

The auscultation device 80 is capable of detecting the sound waves local to the patient's heart and lungs and preferably includes an acoustical coupler and microphone-82, an air tube 84, and a pair of wires 86. The acoustical coupler and microphone 82 is preferably secured to the right side of the palm portion 1 of the palmar side 36 of the glove probe 12, preferably on the first layer 30. The acoustical coupler and microphone 82 is capable of collecting and amplifying sound waves in relative close proximity to the acoustical coupler and microphone. The air tube 84 includes a first end 84a and a second end 84b. The first end 84a of the air tube 84 is preferably connected to the acoustical coupler and microphone 82 and the second end 84b is adaptable for connection with a stethoscope. The air tube 84, thus when connected to a stethoscope, extends between and provides audio communication between the acoustical coupler and microphone 82 and the stethoscope. The pair of wires 86 extend between and electrically connect the acoustical coupler and microphone 82 and the female plug 48. The auscultation device 80 is preferably made of parts similar, or identical, to parts of the EG Company microphone 9445 from the Electrical Gold Co. Of Scottsdale, Ariz.

The glove probe 12 is manufactured by securing, by any suitable means, the wires, sensors, and other components to a glove, preferably made of cloth (i.e., the first layer 30). It should be noted that the wires and/or sensors could be made using flexible circuit technology, such as by using a conductive printable ink. The components of the glove probe 12 which do not extend past the second layer 32 are then covered by the second layer in a suitable manner, such as by spraying or dip coating.

The cable 14 includes a first male plug 14a (FIG. 3), which plugs into male receptors on the female connection plug 48 on the glove probe 12, and a second male plug 14b (FIG. 4), which plugs into male receptors on a female connection plug 19 on the interface unit 20. The cable 14 (FIG. 1) preferably includes a plurality of electrical wires and air tubes which extend between plugs 14a and 14b to provide electrical, audio, and fluid communication between the glove probe 12 and the interface unit 20 when the male plugs 14a (FIG. 3) and 14b (FIG. 4) are plugged into their respective female connection plugs 48 (FIG. 3) and 19 (FIG. 4).

The interface unit 20 (FIG. 1) preferably includes an EKG circuit board 21 (FIG. 4) for receiving EKG currents detected by the sensors 40a-40g, a blood pressure circuit board 23 for receiving systolic and diastolic blood pressure and pulse rate signals from the blood pressure device 54, a temperature circuit board 25 for receiving temperature signals from the temperature device 64 and a % $O_2$ circuit board for receiving % $O_2$ signals from the % $O_2$ device 70. The EKG circuit board 21 is capable of amplifying the EKG currents from the sensors 40a-40g and converting the EKG currents to at least a plurality of EKG analog outputs. The blood pressure circuit board 23 is capable of (i) converting the systolic blood pressure signals to a systolic blood pressure analog output, (ii) the diastolic blood pressure signals to a diastolic blood pressure analog output, and (iii) the pulse rate signals to a pulse rate analog output. The blood pressure circuit board 23 includes a source of inflation fluid, such as an air pump 23a, for supplying a source of inflation fluid for the air bladder 56, and an acoustical sensor (not shown) for detecting the systolic and diastolic blood pressure and pulse rate signals. The pump 23a is in fluid communication with the air bladder 56 (FIG. 2) via the air tube 60, cable 14 (FIG. 1) and air conduit 17 (FIG. 4), which extends between and provides fluid and audio communication between the female connection plug 19 of the cable 14 and the blood pressure circuit board 23. The temperature circuit board 25 converts the temperature signals to a temperature analog output. The % $O_2$ circuit board 27 converts the % $O_2$ signals to a % $O_2$ analog output. The interface unit 20 also includes an audio amp 29 for amplifying the sound waves received from the auscultation device 80 (FIG. 2).

The interface unit 20 further includes a first analog to digital converter 31 for converting the EKG analog outputs to an EKG digital data stream, a second analog to digital converter 33 for converting (i) the systolic blood pressure analog output to a systolic blood pressure digital data stream, (ii) the diastolic blood pressure analog output to a diastolic blood pressure digital data stream, and (iii) the pulse rate analog output to a pulse rate digital data stream, a third analog to digital converter 35 for converting the temperature analog output to a temperature digital data stream, a fourth analog to digital converter 37 for converting the % $O_2$ analog output to a % $O_2$ digital data stream, and a fifth analog to digital converter 41 for converting the sound waves from the first audio amp 29 to a sound digital data stream.

The interface unit 20 further includes a multiplexer 45 for combining the digital data streams from the analog to digital converters 31-37 and 41 to a combined digital data stream. The combined digital data stream can then be conveyed to the PC 24 via a first port 47, or to the command center 22 (FIG. 1) by satellite connection B via a modem, or by radio wave connection C via the port 47, or to the command center 22 by telephone wire, or fiber, A via telephone modem 51 (FIG. 4) and a second port 53 (FIG. 4). The digital data streams from the interface unit 20 are then converted or interpreted into readable diagnostic information in the command center 22 or the PC 24. This circuitry enables the glove probe 12 and the interface unit 20 to be provided at a reasonable cost. The multiplexer 45 also communicates with a control panel and indicator circuit board 55.

The interface unit 20 further includes a speaker/microphone 61 which communicates with the multiplexer 45, via a second audio amp 63 and a sixth analog to digital converter 65, to enable a medical professional in the command center 22 to communicate orally with the persons in relative close proximity to the speaker/microphone.

The interface unit 20 includes a third port 71 for receiving and transmitting EKG currents detected by sensors 40a-40g to an EKG readout apparatus 26a (FIG. 1) where the EKG currents will be converted or interpreted into readable diagnostic information. The interface unit 20 further includes a fourth, fifth and sixth port 73, 75 and 77, respectively, for receiving and transmitting the analog outputs from the blood pressure circuit board 23, the temperature circuit board 25 and the % $O_2$ circuit board 27, respectively, to a blood pressure and pulse readout apparatus 26b, a temperature readout apparatus 26c, and a % $O_2$ readout apparatus 26d where the analog outputs will be converted or interpreted into readable diagnostic information.

The interface unit 20 also includes a power supply 81 which supplies power, via power supply distributor 83, to all of the components of the interface unit. The interface unit 20 also preferably includes a battery pack 85 and a battery charger port 87.

The interface unit further includes an optical isolator 89 for electrically isolating the entire interface unit 20 and glove probe 12 from any destructive and damaging currents which might be encountered from external communication links.

The manner of operation of the system 10 will now be described. The patient places the glove probe 12 over his or her right hand so that each of the patient's fingers are received within a respective one of the phalange portions 5-13. The glove probe 12 can then preferably be tightened around the patient's wrist by any suitable means such as a Velcro strap. The glove probe 12 is then connected to interface unit 20 by cable 14.

EKG Diagnostic Information

To obtain EKG diagnostic information, the palmar side 36 of the glove probe 12 is placed over the patient's chest area proximate to the patient's heart. The sensors 40a-40g are located at strategic positions on the glove probe 12, as described above, to enable a plurality of leadwire combinations to detect a plurality of standard leads when the glove probe 12 is placed over the patient's left breast. Some exemplary leadwire combinations are as follows:

I. Five-Leadwire Scenario:

With the glove probe 12 placed in a normal manner over the left breast, it is believed that at least the following leadwires are possible:

LL acting leadwire: Sensor 40a on the tip portion of the pinky finger phalange 13 is positioned under the left breast.

RL leadwire: Sensor 40e on the right wrist.

LA acting lead: Sensor 40c on the tip portion of the index finger phalange 7 is positioned above the left breast at the left shoulder quadrant.

RA acting leadwire: Sensor 40f on the tip portion of the thumb phalange 5 is positioned above and into the right shoulder quadrant.

C leadwire: Sensor 40b on the palm portion is positioned at the right sternal border.

With the glove probe 12 positioned in the five leadwire scenario, it is believed that the following lead readings are possible: Lead 1, Lead 2, Lead 3, AVR and AVL.

II. Alternate Five-Leadwire Scenario (Yields a More Dynamic Waveform Reading):

With the glove probe 12 rotated from the normal left breast position of the five leadwire scenario by 10 to 15 degrees toward the right breast and with the patient's free left wrist pressed against the dorsal surface 38 of the glove probe, it is believed that at least the following leadwires are possible:

LL leadwire: Sensor 40g on the dorsal surface 38 of the glove probe 12 is positioned against the patient's left wrist.

RL leadwire: Sensor 40e on the right wrist.

LA acting leadwire: Sensor 40c on the tip portion of the index finger phalange 7 is positioned above the left breast at the left shoulder quadrant.

RA leadwire: Sensor 40f on the tip portion of the thumb phalange 5 is positioned above and into the right shoulder quadrant.

C leadwire: Sensor 40b on the palm portion is positioned at the right sternal border.

III. Seven-Leadwire Scenario:

With the glove probe 12 placed in the normal left breast position of the five leadwire scenario and the patient's left wrist pressed against the dorsal surface 38 of the glove probe, it is believed that at least the following leadwires are possible:

LL leadwire: Sensor 40g on the dorsal surface 38 of the glove probe 12 is positioned against the patient's left wrist.

V2 leadwire: Sensor 40d on the base portion of the pinky finger phalange 13 is positioned in the V2 position.

V4 leadwire: Sensor 40a on the tip portion of the pinky finger phalange 13 is positioned in the V4 position.

RL leadwire: Sensor 40e on the right wrist.

LA acting leadwire: Sensor 40c on the tip portion of the index finger phalange 7 is positioned above the left breast at the left shoulder quadrant.

RA leadwire: Sensor 40f on the tip portion of the thumb phalange 5 is positioned above and into the right shoulder quadrant.

C leadwire: Sensor 40b on the palm portion is positioned at the right sternal border.

With the glove probe 12 positioned in the seven leadwire scenario, it is believed that at least the following lead readings are possible: Lead 1, Lead 2, Lead 3, AVR, AVL, V2 and V4.

IV. Three-Leadwire Scenarios:

It is believed that the following leadwires are also possible:

Lead 1:

Positive leadwire: Sensor 40c on the tip portion of the index finger phalange 7 is positioned above the left breast at the left shoulder quadrant.

Negative leadwire: Sensor 40f on the tip portion of the thumb phalange 5 is positioned above and into the right shoulder quadrant.

Ground leadwire: Sensor 40e on the right wrist.

Lead 2:

Positive leadwire: Sensor 40a on the tip portion of the pinky finger phalange 13 is positioned under the left breast towards the V6 position.

Negative leadwire: Sensor 40f on the tip portion of the thumb phalange 5 is positioned above and into the right shoulder quadrant.

Ground leadwire: Sensor 40e on the right wrist.

Optional Lead 2:

Positive leadwire: Sensor 40g on the dorsal surface 38 of the glove probe 12 is positioned against the patient's left wrist.

Negative leadwire: Sensor 40c on the tip portion of the index finger phalange 7 is positioned above the left breast at the left shoulder quadrant.

Ground leadwire: Sensor 40e on the right wrist.

Lead 3:

Positive leadwire: Sensor 40a on the tip portion of the pinky finger phalange 13 is positioned under the left breast towards the V6 position.

Negative leadwire: Sensor 40c on the tip portion of the index finger phalange 7 is positioned above the left breast at the left shoulder quadrant.

Ground leadwire: Sensor 40e on the right wrist.

Optional Lead 3:

Positive leadwire: Sensor 40g on the dorsal surface 38 of the glove probe 12 is positioned against the patient's left wrist.

Negative leadwire: Sensor 40c on the tip portion of the index finger phalange 7 is positioned above the left breast at the left shoulder quadrant.

Ground leadwire: Sensor 40e on the right wrist.

MCL1 Lead:

Negative leadwire: Sensor 40c on the tip portion of the index finger phalange 7 is positioned above the left breast at the left shoulder quadrant.

Positive leadwire: Sensor 40b on the palm portion is positioned at the right sternal border.

Ground leadwire: Sensor 40e on the right wrist.

MCL4 Lead:

Negative leadwire: Sensor 40c on the tip portion of the index finger phalange 7 is positioned above the left breast at the left shoulder quadrant.

Positive leadwire: Sensor 40a on the tip portion of the pinky finger phalange 13 is positioned in the V4 position.

Ground leadwire: Sensor 40e on the right wrist.

It should be noted that other EKG scenarios can be accomplished at the discretion of the command center 22. Such options are available since the following glove member positions relate to electrical heart activity as below:

G (ground) leadwire: Right wrist (sensor 40e)+
+ (positive) leadwire: left wrist (sensor 40g)
− or + leadwire: Index finger phalange 7 tip (sensor 40c)
− (negative) leadwire: Thumb phalange 5 tip (sensor 40f).

It should also be noted that, in the event that distortion of the EKG waveform occur due to misplacement of the glove EKG sensors 40a-g, correction of such can be accomplished using waveform modification circuits located at the command center 22. Such waveform modification circuitry accomplishes distortion correction utilizing waveshaping techniques which filter, compare, and re-shape into readable data.

The EKG currents, or leads, detected from the sensors 40a-40g are transmitted to the female connection plug 48, and through the cable 14 to the interface unit 20 where they can be sent to the command center 22 or PC 24 in a digital data stream, or to the EKG readout apparatus 26a, as discussed above.

Blood Pressure and Pulse Rate Diagnostic Information

To obtain blood pressure and pulse rate diagnostic information, when the glove probe 12 wrist portion 3 is tightened around the patient's wrist, the air bladder 56 is ready to accept air pressure from the pump 23a in the blood pressure circuit board 23. The air pump 23a then transmits inflation fluid, such as air, via the conduit-17, cable 14 and air tube 60, to the air bladder 56 to inflate the air bladder. Inflation of the air bladder 56 obliterates the radial artery. As the air bladder 56 releases the inflation fluid, pulse sound waves are acoustically picked-up by acoustical coupler 58 and are sent over the air tube 60 to the female connection plug 48, and through the cable 14 to the interface unit 20 where they can be sent to the command center 22 or PC 24 in a digital data stream, or to the blood pressure and pulse rate readout 26b, as discussed above.

Body Temperature Diagnostic Information

To obtain body temperature diagnostic information, the middle finger phalange portion 9 of the glove probe 12 is placed under the patient's tongue for a period of time sufficient to receive temperature signals from the thermistor 66, preferably about one minute. The temperature signals from the temperature device 64 can be transmitted to the female connection plug 48, and through the cable 14 to the interface unit 20 where they can be sent to the command center 22 or PC 24 in a digital data stream, or to the temperature readout apparatus 26c, as discussed above.

% $O_2$ Diagnostic Information

To obtain % $O_2$ diagnostic information, the red LED emitter 72 (FIG. 2) emits red and infra-red light toward the LED sensor 74. When the light from the LED emitter 72 is passed through the patient's finger (non-painted finger nails only) at the nail, the LED sensor 74 detects the color light waves present. These signals are translated from light intensity and color quality to oxygen levels. More oxygen yields a light red blood while less oxygen produces a darker red to purple blood. It should be noted that pulse rate can also be ascertained from these readings.

The % $O_2$ signals from the % $O_2$ device 70 are then sent to the female connection plug 48, and through the cable 14 to the interface unit 20 where the % $O_2$ signals can be sent to the command center 22 or PC 24 in a digital data stream, or to the % $O_2$ readout apparatus 26d, as discussed above.

Auscultation Diagnostic Information

To listen to the heart and lungs of the patient, the glove probe 12 is moved over the patient's body to enable the acoustical coupler and microphone 82 to pick up, or hear, sound waves from the patient's heart and lungs, much like a stethoscope would. The sound waves are then transmitted to the female connection plug 48, via the pair of wires 86, and then through the cable 14 to the interface unit 20, where they can be sent to the command center or PC 24, in a digital data stream as described above. Alternatively, the sound waves from the acoustical coupler of the acoustical coupler and microphone 82 could also be conducted via air tube 84 to a stethoscope 26e, as described above.

Oral Communication

To communicate orally with a remote location, such as the command center 22, the speaker/microphone 61 can transmit and receive sound waves as described above. This allows individuals proximate to the interface unit 20 to be able to communicate with individuals (i.e., medical professionals) at the remote location, such a doctors, to transmit and receive oral information such as physical observations and medical advice, such as that based on the analysis at the remote location on information received from the system 10 and probe 20. It should be noted that the interface unit 20 may not be able to transmit or receive sound waves via speaker/microphone 61 when processing diagnostic information from the EKG diagnostic device, the blood pressure device 54, the temperature device 64, the % $O_2$ device 70 and/or the auscultation device 80.

While the best modes for carrying out the invention have been described in detail, those familiar with the art to which the invention relates will appreciate other ways of carrying out the invention defined by the following claims. For instance, the placement of the diagnostic devices on the glove probe 12 and/or specific design of the diagnostic devices could vary from that described above. For instance, the EKG device could have more or fewer sensors or the sensors could be located differently than that described above. Moreover, the glove probe could be adapted to be worn on the patient's left hand.

What is claimed is:

1. A method of obtaining and transmitting medical diagnostic information from a remote location, said method comprising:
    collecting electrical medical diagnostic information from a first person at a first location via a diagnostic probe, the diagnostic probe comprising a member wearable on a person's hand and contoured to at least a portion of a person's hand and having at least one diagnostic device and a surface configured to conform to a portion of the palm of the hand, the surface having at least one sensor thereon, wherein the sensor has a sensing portion located on the surface;
    positioning the diagnostic probe on the first person's hand to sense diagnostic signals from a person for collecting the medical diagnostic information from the first person at the first location, wherein the medical diagnostic information comprises EKG information;
    transmitting the diagnostic information via an interface unit in electrical communication with the member from the first location to a second location, the first location being remote from the second location; and
    analyzing the diagnostic information at the second location and transmitting an oral communication from the second location to the first location.

2. The method of claim 1 wherein the communication comprises medical advice pertaining to the first person based on the analysis of the diagnostic device.

3. The method of claim 1 wherein the medical diagnostic information further comprises blood pressure information.

4. The method of claim 3 wherein the medical diagnostic information further comprises temperature and percent $O_2$ information.

5. The method of claim 1 wherein the interface unit comprises a speaker for receiving and transmitting voice signals, the communication comprising voice signals from a second person at the second location.

6. The method of claim 1 wherein a medical professional is at the second location to analyze the diagnostic information and transmit the communication to the first location and the medical professional communicates with the first person to ascertain medical information from the first person prior to the step of collecting at least one piece of medical diagnostic information.

7. The method of claim 1 wherein the diagnostic probe comprises a plurality of diagnostic devices.

8. The method of claim 1 wherein the diagnostic device comprises at least one EKG sensor for collecting the EKG information.

9. The method of claim 1 wherein the oral communication is transmitted directly from the second location to the first location.

10. The method of claim 1 wherein the diagnostic probe is configured to send diagnostic signals from a person when placed on the person's chest.

11. The method of claim 1 wherein positioning the diagnostic device on the first person's hand further comprises placing the diagnostic device on the first person's hand to sense diagnostic signals from a person.

12. A method of obtaining and transmitting medical diagnostic information from a remote location, said method comprising:
    collecting electrical medical diagnostic information from a first person at a first location via a diagnostic probe, the diagnostic probe comprising a member wearable on a person's hand and contoured to at least a portion of a person's hand and having at least one diagnostic device and a surface configured to conform to a portion of the palm of the hand, the surface having at least one sensor thereon, wherein the sensor has a sensing portion located on the surface;
    positioning the diagnostic probe on a second person's hand to sense diagnostic signals from the first person, wherein the second person wears the member and collects the diagnostic information from the first person at the first location;
    transmitting the diagnostic information via an interface unit in electrical communication with the member from the first location to a second location, the first location being remote from the second location; and
    analyzing the diagnostic information at the second location and transmitting an oral communication from the second location to the first location.

13. A method of obtaining and transmitting medical diagnostic information from a remote location, said method comprising:
    collecting electrical medical diagnostic information from a first person at a first location via a diagnostic probe, the diagnostic probe comprising a member wearable on a person's hand and contoured to at least a portion of a person's hand and having a plurality of diagnostic devices and a surface configured to conform to a portion of the palm of the hand, the surface having at least one sensor thereon, wherein the sensor has a sensing portion located on the surface and the member comprises a glove that corresponds to at least a substantial portion of a person's hand such that said member is capable of being worn on a person's hand, the glove having a plurality of diagnostic sensors adapted to face away from the hand to sense diagnostic signals from the person;
    positioning the diagnostic probe on the first person's hand to sense diagnostic signals from a person for collecting the medical diagnostic information from the first person at the first location, wherein the diagnostic information comprises a plurality of diagnostic information obtained from the plurality of diagnostic devices, the diagnostic devices comprising an EKG diagnostic device, a blood pressure and pulse diagnostic device, and a temperature device;
    transmitting the diagnostic information via an interface unit in electrical communication with the member from the first location to a second location, the first location being remote from the second location; and analyzing the diagnostic information at the second location and transmitting an oral communication from the second location to the first location.

14. A method of obtaining and transmitting medical diagnostic information from a remote location, said method comprising:

collecting EKG diagnostic information from a first person at a first location, wherein a diagnostic probe comprising a member contoured to at least a portion of a person's hand, having a shape that corresponds to at least a substantial portion of a person's hand such that the member is capable of being worn on a person's hand, has at least one diagnostic device and a surface configured to conform to a portion of the palm of the hand, the surface having at least one sensor thereon, wherein the sensor has a sensing portion located on the surface;

placing the diagnostic probe on the first person to sense diagnostic EKG signals from a person for collecting the EKG diagnostic information from the first person at the first location;

transmitting the diagnostic information via an interface unit in electrical communication with the member from the first location to a second location, the first location being remote from the second location; and transmitting an oral communication from the second location to the first location, wherein the communication comprises medical advice pertaining to the first person based on the analysis of the diagnostic device.

15. The method of claim 14 wherein the member comprises a plurality of diagnostic devices and the diagnostic information comprises a plurality of diagnostic information obtained from the plurality of diagnostic devices, the diagnostic devices comprising an EKG diagnostic device, a blood pressure and pulse diagnostic device, and a temperature device.

16. The method of claim 14 wherein the member comprises a glove.

17. The method of claim 14 wherein the member comprises at least two phalange portions having EKG sensors thereon.

18. A method of obtaining and transmitting medical diagnostic information from a remote location, said method comprising:

collecting medical diagnostic information from a first person at a first location via a diagnostic probe, the diagnostic probe comprising a member contoured to at least a portion of a person's hand, having a surface including one or more sensors and configured to conform to a portion of the palm of the hand, the sensors having a sensing portion located on the surface, and having at least one diagnostic device for placing over the first person to sense diagnostic signals from the first person for collecting medical diagnostic information from the first person at the first location, wherein a second person wears the member and collects the diagnostic information from the first person;

transmitting the diagnostic information from the first location to a second location, the first location being remote from the second location; and further comprising analyzing the diagnostic information at the second location.

19. The method of claim 18 wherein the member has a shape that corresponds to at least a substantial portion of a person's hand such that the member is capable of being worn on a person's hand.

20. The method of claim 19 wherein the member comprises a plurality of diagnostic devices.

21. A method of obtaining and transmitting medical diagnostic information from a remote location, said method comprising:

collecting EKG information from a first person at a first location, wherein a diagnostic probe comprising a member having a shape that corresponds to at least a substantial portion of a person's hand such that the member is capable of being worn on a person's hand and having at least one diagnostic device capable of sensing diagnostic signals from a person and a surface configured to conform to a portion of the palm of the hand, the surface having at least one sensor thereon and the sensor having a sensing portion located on the surface, is provided for collecting the EKG information from the first person at the first location;

transmitting the EKG information via an interface unit in electrical communication with the member from the first location to a second location, the first location being remote from the second location; and transmitting an oral communication from the second location to the first location.

22. A method of obtaining and transmitting medical diagnostic information from a remote location, said method comprising:

collecting EKG diagnostic information from a first person at a first location, wherein a diagnostic probe comprising a member contoured to at least a portion of a person's hand, having a shape that corresponds to at least a substantial portion of a person's hand such that the member is capable of being worn on a person's hand, and further having at least one diagnostic device capable of sensing diagnostic EKG signals from a person and a surface configured to conform to a portion of the palm of the hand, the surface having at least one sensor thereon, wherein the sensor has a sensing portion located on the surface, is provided for collecting the EKG diagnostic information from the first person at the first location, wherein the member comprises a glove;

transmitting the EKG diagnostic information via an interface unit in electrical communication with the member from the first location to a second location, the first location being remote from the second location; and transmitting an oral communication from the second location to the first location.

23. The method of claim 22 wherein the member comprises at least two phalange portions having sensors thereon.

24. A method of obtaining and transmitting medical diagnostic information from a remote location, said method comprising:

collecting electrical medical diagnostic information from a first person at a first location via a diagnostic probe, the diagnostic probe comprising a member wearable on a person's hand and contoured to at least a portion of a person's hand and having at least one diagnostic device and a surface configured to conform to a portion of the palm of the hand, the surface having at least one sensor thereon, wherein the sensor has a sensing portion located on the surface;

positioning the diagnostic probe on the first person's hand;

placing the diagnostic probe on the person's chest to sense diagnostic signals from a person for collecting the medical diagnostic information from the first person at the first location;

transmitting the diagnostic information via an interface unit in electrical communication with the member from the first location to a second location, the first location being remote from the second location; and analyzing the diagnostic information at the second location and transmitting an oral communication from the second location to the first location.

25. A method of obtaining and transmitting medical diagnostic information from a remote location, said method comprising:

collecting electrical medical diagnostic information from a first person at a first location, wherein a diagnostic probe comprising a member wearable on a person's hand and contoured to at least a portion of a person's hand and having at least one diagnostic device to sense diagnostic signals from the first person is provided for collecting the medical diagnostic information from the first person at the first location, the diagnostic device being placed on the first person's chest to collect the medical diagnostic information;

transmitting the diagnostic information via an interface unit in electrical communication with the member from the first location to a second location, the first location being remote from the second location; and analyzing the diagnostic information at the second location and transmitting an oral communication from the second location to the first location, wherein a medical professional is at the second location to analyze the diagnostic information and transmit the communication to the first location, and wherein the medical professional communicates with the first person to ascertain medical information from the first person prior to the step of collecting at least one piece of medical diagnostic information.

* * * * *